(12) United States Patent
Mori et al.

(10) Patent No.: US 9,549,790 B2
(45) Date of Patent: Jan. 24, 2017

(54) SCANNING JIG

(71) Applicant: GC CORPORATION, Tokyo (JP)

(72) Inventors: Katsuya Mori, Tokyo (JP); Naoto Fujii, Tokyo (JP)

(73) Assignee: GC CORPORATION, Tokyo (JP)

( * ) Notice: Subject to any disclaimer, the term of this patent is extended or adjusted under 35 U.S.C. 154(b) by 172 days.

(21) Appl. No.: 14/401,654

(22) PCT Filed: May 15, 2013

(86) PCT No.: PCT/JP2013/063596
§ 371 (c)(1),
(2) Date: Nov. 17, 2014

(87) PCT Pub. No.: WO2014/002632
PCT Pub. Date: Jan. 3, 2014

(65) Prior Publication Data
US 2015/0140514 A1 May 21, 2015

(30) Foreign Application Priority Data
Jun. 26, 2012 (JP) .................. 2012-142776

(51) Int. Cl.
*A61C 8/00* (2006.01)
*A61C 13/235* (2006.01)
(Continued)

(52) U.S. Cl.
CPC ........... *A61C 8/0001* (2013.01); *A61C 9/0053* (2013.01); *A61C 13/235* (2013.01); *A61C 13/34* (2013.01)

(58) Field of Classification Search
CPC ...... A61C 13/235; A61C 8/0081; A61C 13/34
See application file for complete search history.

(56) References Cited

U.S. PATENT DOCUMENTS

| 4,758,160 A | 7/1988 | Ismail |
| 5,954,506 A | 9/1999 | Tanaka |

(Continued)

FOREIGN PATENT DOCUMENTS

| DE | 102006021476 B3 | 10/2007 |
| JP | 2003190187 A | 7/2003 |

(Continued)

OTHER PUBLICATIONS

International Search Report Appln. No. PCT/JP2013/063596; Dated Aug. 13, 2013.

*Primary Examiner* — Michael Kahelin
(74) *Attorney, Agent, or Firm* — Ladas & Parry LLP

(57) ABSTRACT

Provided is a scanning jig capable of improving replacement accuracy of three-dimensional data. Provided is a scanning jig 10 for attaching to an analog 20 embedded in a model or to an artificial tooth root 30 embedded inside an oral cavity, the scanning jig including: a main body 11 formed in a bottomed cylindrical shape provided with a bottom to one end portion; a fixation member 12 of which one end side is inserted inside the cylindrical shape of the main body and the other end side is fixated to the analog or the artificial tooth root; and a magnet 13 arranged inside the cylindrical shape of the main body, wherein the main body is not provided with a hole or a groove on one end surface on a bottom side of the bottomed cylindrical shape, and the end surface is provided with an inclined surface.

2 Claims, 14 Drawing Sheets

(51) Int. Cl.
*A61C 9/00* (2006.01)
*A61C 13/34* (2006.01)

(56) References Cited

U.S. PATENT DOCUMENTS

| | | |
|---|---|---|
| 2005/0019728 A1 | 1/2005 | Rostagno et al. |
| 2009/0123887 A1 | 5/2009 | Brajnovic |
| 2012/0141951 A1 | 6/2012 | Bellanca et al. |

FOREIGN PATENT DOCUMENTS

| | | |
|---|---|---|
| JP | 2007527284 A | 9/2007 |
| JP | 2008142528 A | 6/2008 |
| JP | 2009101124 A | 5/2009 |
| JP | 2011504390 A | 2/2011 |
| JP | 2012517308 A | 8/2012 |
| WO | 2007/128263 A1 | 11/2007 |
| WO | 2010097214 A1 | 9/2010 |
| WO | 2010108919 A2 | 9/2010 |
| WO | 2012126475 A1 | 9/2012 |

US 9,549,790 B2

SCANNING JIG

BACKGROUND OF THE INVENTION

Field of the Invention

The present invention relates to a scanning jig which is a member used in the field of dentistry for specifying a position of an embedded artificial tooth root (may be generally called an implant fixture or an implant body) to obtain a three-dimensional data.

Description of the Related Art

In the field of dentistry, a so-called dental implant technique has been largely applied as a prosthesis method for a defective tooth. The application of implant with the dental implant technique has more advantages compared with a conventional dental prosthesis, since it can make a state closer to that of a natural tooth.

A treatment with the implant is generally carried out by the following processes. That is: a hole is created to the jawbone at the defective site where the implant is to be applied; an artificial tooth root is embedded thereto; after the embedded artificial tooth root is sufficiently joined to the jawbone, an abutment which is a member for fixating a dental prosthesis is attached to the embedded artificial tooth root; then the dental prosthesis is arranged to the abutment.

The abutment is designed and produced individually for each patient in conformity with the depth and direction of the embedded artificial tooth root, and a state of the patient's oral cavity. In this regard, since the abutment has to be produced in conformity with a state of the artificial tooth root actually embedded, it is needed to know how the artificial tooth root is embedded before the abutment is produced. To this end, with an impression coping, information of the posture (depth and direction) of the artificial tooth root being embedded is transferred to an analog model which is a plaster model including an analog (a replica of the artificial tooth root). From the analogue model, the information of the artificial tooth root is obtained, whereby the abutment is produced.

Recently, the abutment is produced by means of an automatic cutting processing with three-dimensional shape data, and even an abutment having a complicated shape can be produced with a good accuracy. Therefore, in order to obtain the three-dimensional shape data for processing, it is needed to obtain a three-dimensional shape data including shapes of required parts in a person's oral cavity, an outer shape of the analog model, and postural information such as the depth and direction of the artificial tooth root.

However, among them, since the postural information (depth and direction) of the artificial tooth root is transferred to the analog and the analog is embedded inside the analog model, it is not possible to obtain the postural information of the artificial tooth root as a three-dimensional shape data as it is. On this issue, a scanning jig attached to the embedded analog in a manner to extend the analog, thereby being arranged such that one end side thereof projects from the analog model is used. That is, the scanning jig is attached coaxially to the analog, and an end portion of the scanning jig where the analog is not connected is exposed in a manner to project from the analog model. Therefore, it is possible to obtain the direction and positional information of the analog. By measuring three dimensionally the analog model with the scanning jig attached thereto to obtain a three-dimensional shape data, it is possible to obtain the orientation in a longitudinal direction of the analog embedded on an extension line of the scanning jig, and the positional information of the analog from a position of the end portion of the scanning jig (see Patent Document 1 for example).

In this regard, in order to obtain the three-dimensional shape data with an improved accuracy, in the obtained three-dimensional shape data of the analog model including the scanning jig, the three-dimensional shape data of the scanning jig is replaced with a three-dimensional shape data of the scanning jig which is prepared in advance.

Here, the term "scanning jig" is not necessarily widely used in the technical field of the present invention. However, since there is no unified name in the technical field, for a member which corresponds to the scanning jig having functions described above, the member is herein described as the "scanning jig".

CITATION LIST

Patent Literatures

Patent Document 1: U.S. patent application Ser. No. 2009/0123887

SUMMARY OF THE INVENTION

Problems to be Solved by the Invention

In the conventional technique of the scanning jig as described in Patent Document 1, an end surface of the scanning jig on a side projecting from the analog has a hole where a screw is to be inserted or a screw head. With this state, in replacing the three-dimensional shape data of the scanning jig described above, there is a problem with replacement accuracy at a position in the longitudinal direction of the scanning jig, caused by the above configuration of the end surface. Also, an improvement in replacement accuracy of the position relating to a rotational direction (orientation in the rotational direction) of the scanning jig having the longitudinal direction as an axis is desired.

The replacement accuracy in the longitudinal direction and the replacement accuracy in the orientation of the rotational direction as above are important, since they affect the fitting accuracy of the abutment and the artificial tooth root.

Accordingly, considering the above problems, an object of the present invention is to provide a scanning jig capable of improving replacement accuracy of three-dimensional shape data.

Means for Solving the Problems

Hereinafter, the present invention will be described. In order to make the present invention easy to understand, reference numerals given in the accompanying drawings are shown here in parentheses. However, the present invention is not limited to this.

The present invention is a scanning jig (10) for attaching to an analog (20) embedded in a model, or to an artificial tooth root (30) embedded in an oral cavity, the scanning jig including: a main body (11) formed in a bottomed cylindrical shape provided with a bottom to one end portion; a fixation member (12) of which one end side is inserted inside the cylindrical shape of the main body and the other end side is fixated to the analog or the artificial tooth root; and a magnet (13) arranged inside the cylindrical shape of the main body, wherein: the main body is not provided with a hole or a groove on an end surface on a bottom side of the bottomed cylindrical shape; and the end surface is provided with an inclined surface.

In the present invention, for a cylindrical axis direction of the main body, the main body (11) may be, with a posture of being attached to the analog (20) or the artificial tooth root (30), configured such that only one end surface on a side where the bottom is not formed has contact with the analog or the artificial tooth root.

EFFECTS OF THE INVENTION

According to the present invention, after obtaining a three-dimensional shape data with the scanning jig attached to the analog of the analog model, or after obtaining a three-dimensional shape data with the scanning jig attached to the artificial tooth root embedded in an oral cavity, it is possible to improve the replacement accuracy of the scanning jig especially in the longitudinal direction (axial direction), in replacing the portion of the scanning jig in the three-dimensional shape data with a three-dimensional shape data of the scanning jig obtained in advance.

DETAILED DESCRIPTION OF THE INVENTION

Figure 1:
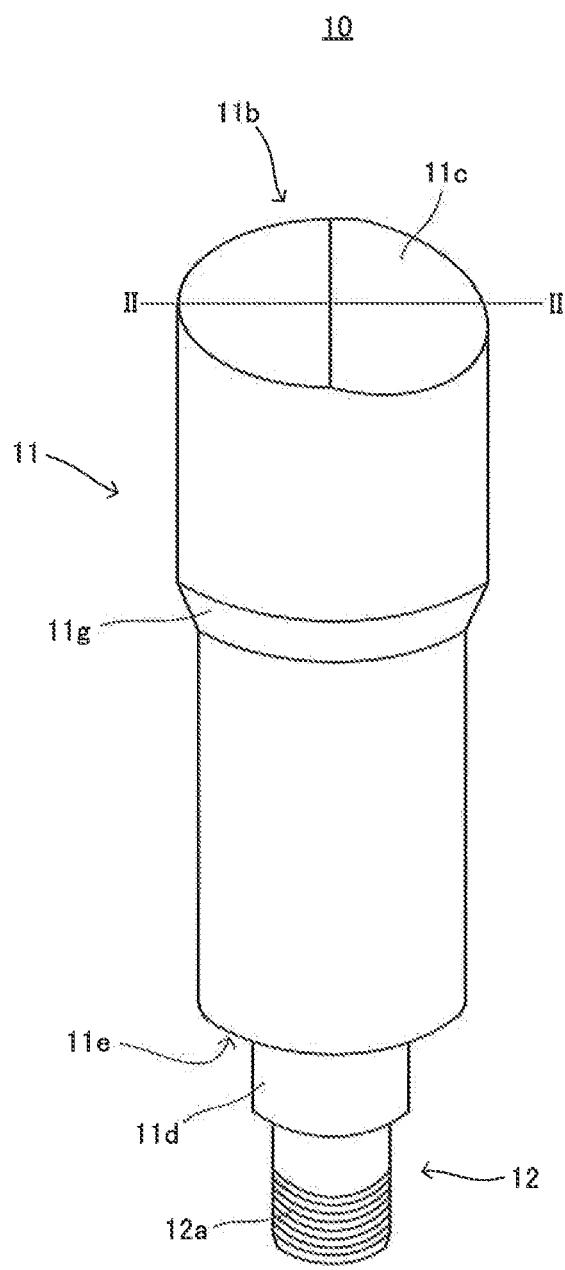
FIG. 1 is a perspective view of a scanning jig according to one embodiment.

The functions and benefits of the present invention described above will be apparent from the following modes for carrying out the invention. Hereinafter, the present invention will be described based on the embodiments shown in the drawings. However, the invention is not limited to these embodiments.

Figure 2:
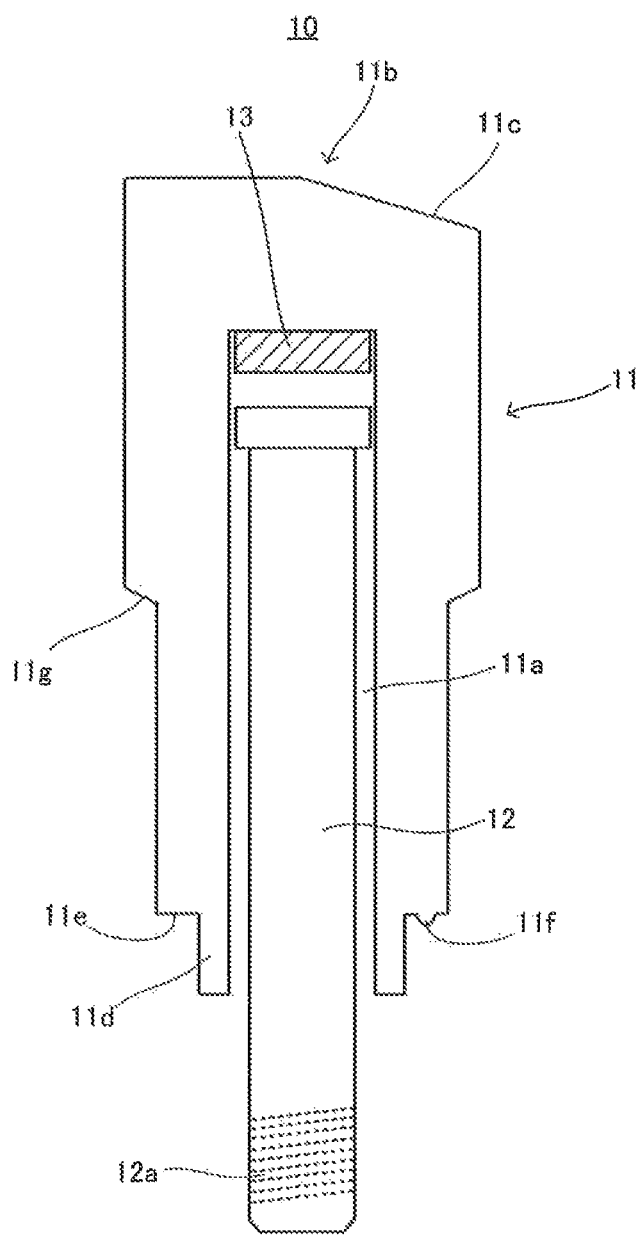
FIG. 2 is a cross-sectional view taken along a line shown by II-II in FIG. 1.

FIG. 1 is a perspective view of an external appearance of a scanning jig 10 according to one embodiment. FIG. 2 is a cross-sectional view taken along a longitudinal direction (axial direction) of the scanning jig including a line shown by II-II in FIG. 1. As can be seen from FIGS. 1 and 2, the scanning jig 10 includes a main body 11, a fixation member 12, and a magnet 13.

The main body 11 is a member formed in a bottomed cylindrical shape provided with a bottom only to one end side. As shown in FIG. 2, a hollow part 11a is formed inside the main body 11. The hollow part 11a has an enough size and shape to insert a fixation member 12, as described below.

In the main body 11, there is no hole or a groove on an end surface 11b which is an end surface of the bottomed cylindrical shape and on a side configuring one end surface of the scanning jig 10. The main body 11 is configured such that the end surface 11b has a large dimension. Further, an inclined surface 11c is formed to a part of the end surface 11b.

Also, in this embodiment, the main body 11 is formed so as to have different outer diameters between on one end side and on the other end side in the longitudinal direction of the cylindrical shape at a circumference side. A portion where the outer diameters are changed is a taper 11g. In this embodiment, the portion where the outer diameters are changed is formed as a taper. However, the present invention is not limited to this, and may be a level gap in which the outer diameters are rapidly changed.

In end surfaces in the longitudinal direction of the main body 11, an end surface 11e which functions as a position determination means in an axial direction is formed to a side opposite from the end surface 11b where the bottom exists. The side where the end surface 11e is formed includes an opening communicating to the hollow part 11a. Also, a protrusion 11f is provided to a part of the end surface 11e, as a position determination means in rotational direction.

Further, from a part of the end surface 11e where the protrusion 11f is not provided, a fitting part 11d formed in a cylindrical shape is arranged in a manner to extend in a direction extending the main body 11 to the longitudinal direction (axial direction). The fitting part 11d functions as a position determination means in radial direction of the main body 11 as well, and it is formed so as to be inserted to the analog embedded to the analog model, or to a fitted part (see a fitted part 20d in FIG. 6 for example) of the artificial tooth root embedded in an oral cavity, as described below. In this embodiment, the fitting part 11d is provided to a hollow part 11a side of the end surface 11e.

The main body 11 is formed of a metal or a resin being a material having a high processing accuracy and a high accuracy sustention effect. Also, it is preferable that the material does not cause malfunctions to a measuring device. For example, in a case where a measurement is carried out by means of laser light, resins are preferable, and among them, an engineering plastic is most preferable in view of having balance with processing with a high accuracy.

The fixation member 12 is a fixation member arranged inside the hollow part 11a of the main body 11, and in this embodiment, configured by a screw. The fixation member 12 of this embodiment is arranged such that a screw part 12a provided to one end is projected from the main body 11, and the screw part 12a is threaded with a hollow part 20a (see FIG. 6) of the analog or a hollow part 20a (see FIG. 12) of the artificial tooth root. The other end of the fixation member 12 is provided with a screw head.

Also, the fixation member 12 is made of a material to be attracted by a magnet.

The magnet 13 is a magnet arranged to a side closest to the bottom of the bottomed cylindrical shape in the hollow part 11a of the main body 11. The magnet 13 is preferably made of a material difficult to be demagnetized, from a viewpoint that the fixation member 12 is repeatedly used. As the magnet, a permanent magnet is easy to use, and a small magnet but having a strong magnetic flux as much as possible is desired. To this end, rare earth magnets such as SmCo based magnet and NdFe based magnet are preferable. Also, the shape of the magnet is normally in a cylindrical shape or a columnar shape, depending on conditions to use.

With the scanning jig 10 as described above, it is possible to attach the scanning jig 10 to the analog in the analog model or the artificial tooth root in the oral cavity, as described below. Then, the scanning jig 10 is arranged in a manner to project from the analog model or a gum in a direction extending the analog embedded in the analog model or the artificial tooth root in the oral cavity. By measuring the scanning jig at the projected portion, it becomes possible to obtain the embedded posture of the analog or the artificial tooth root (see FIGS. 8 and 12).

Also, with the scanning jig 10, it is possible to form a large dimension of the end surface of the scanning jig 10, including the inclined surface 11c, without having a hole or a groove on the end surface 11b. As described later, this makes it possible to improve the replacement accuracy in the longitudinal direction (axial direction) of the scanning jig 10 in replacing an obtained shape measurement data from a three-dimensional measurement of the scanning jig attached to the analog model or in the oral cavity, with a three-dimensional data of the scanning jig prepared in advance. Conventionally, the end surface of the scanning jig cannot have a large dimension, since it is formed in an annular shape with a hole or there is a groove of a screw head for example. Since the replacement of the data is carried out with reference to the surface to be replaced, if the surface does not have a large dimension, recognition accuracy of the surface is degraded, whereby the replacement accuracy is degraded. In contrast, the scanning jig 10 can have a large dimension at the end surface 11b including the inclined surface 11c as described above, thus it is possible to improve the replacement accuracy of the position in the longitudinal direction. Regarding other directions than the longitudinal direction of the scanning jig 10, since an outer peripheral surface of the main body 11 has a sufficient dimension, a replacement is carried out with a good accuracy.

Also, by providing the inclined surface 11c to the end portion 11b, it is possible to show the orientation of the scanning jig 10 in the rotational direction centering the rotation axis of the scanning jig 10 (cylindrical axis of the main body 11). This also makes it possible to improve the replacement accuracy in the rotational direction. In addition, by changing the configuration of the inclined surface 11c depending on kinds of the artificial tooth root for example, it is also possible to obtain information regarding what kind of artificial tooth root is applied. Therefore, inclining angle, dimension of the inclined surface, and the configuration of the inclined surface are not limited to this embodiment but can be adequately changed.

Also, since it is possible to arrange the main body 11 only by putting it on the fixation member 12, and the main body 11 and the fixation member 12 are arranged stably with the magnet 13, it is possible to maintain the attachment stably with an easy disposition.

Further, as described more specifically later, since each of the positions of the main body 11 of in the axial direction, in the rotational direction, and in the radial direction is determined by means of one contacting portion (position determination means) having contact with the analog or the artificial tooth root, each position determination is not affected by the other portions, whereby it is possible to improve the accuracy of position determination. In specific, regarding the axis direction of the main body 11, only the end surface 11e as the position determination means in axis direction has contact with the analog or the artificial tooth root to determine the position. That is, the end surface of the fitting portion 11d does not have contact with the analog 20 or the artificial tooth root 30, and the main body 11 and the magnet 13 do not have contact with the fixation member 12 in the axial direction (see FIGS. 8 and 12).

Regarding the rotational direction of the main body 11, only the protrusion 11f as the position determination means in rotational direction regulates the positional relationship with the analog or the artificial tooth root.

Also, regarding the radial direction of the main body 11, only the outer peripheral portion of the fitting part 11d as the position determination means in radial direction determines the positional relationship with the analog or the artificial tooth root.

Figure 3:
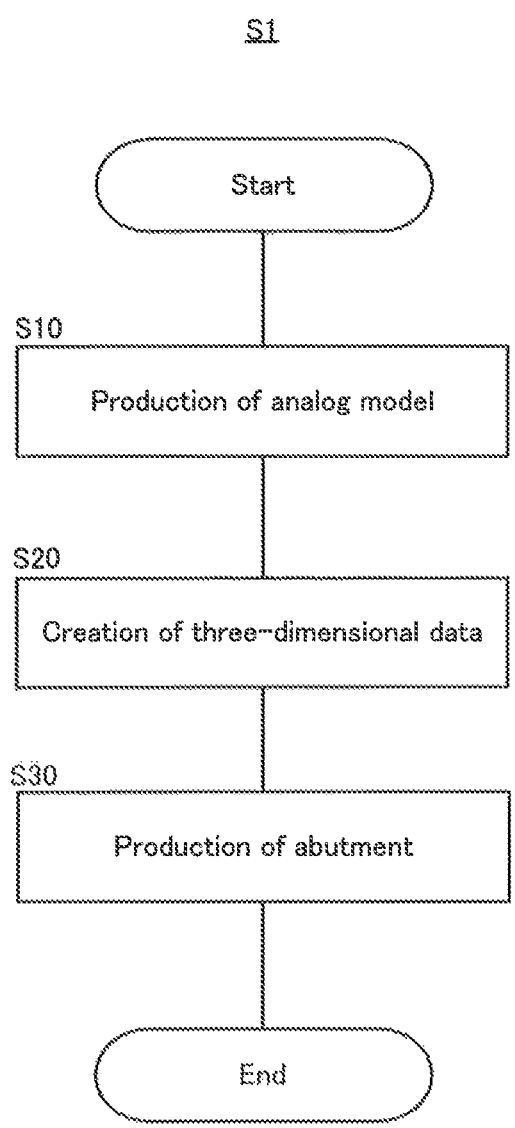
FIG. 3 is a flowchart to explain manufacturing steps of an abutment.

Next, an abutment manufacturing method S1 which is one example of a method for manufacturing an abutment using the scanning jig 10 will be described. This method is a manufacturing method of an abutment using an analog model. FIG. 3 shows a flow of the abutment manufacturing method S1. As can be seen from FIG. 3, the abutment manufacturing method S1 includes an analog model producing step S10, a three-dimensional data creating step S20, and an abutment producing step S30. Each step will be described hereinafter.

Figure 4:
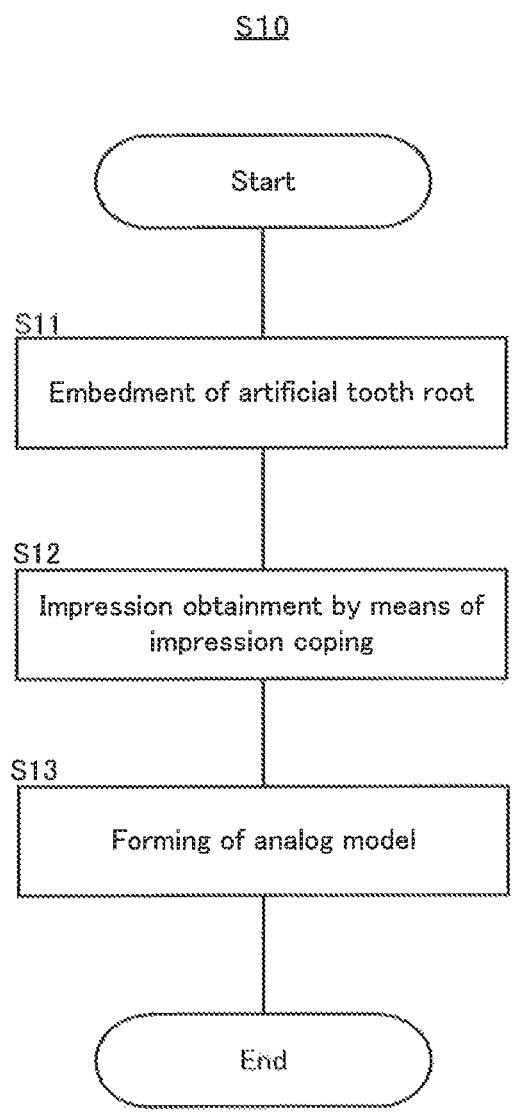
FIG. 4 is a flowchart to explain a producing step of an analog model.

The analog model producing step S10 is a step of producing an analog model in which the analog 20 is embedded. A known step can be applied to this step. FIG. 4 shows an example of flow of the analog model producing step S10. That is, the analog model producing step S10 includes an artificial tooth root embedding step S11, an impression obtaining step S12 by means of an impression coping, and an analog model forming step S13.

The artificial tooth root embedding step S11 is a step of creating a hole to embed an artificial tooth root to the jawbone at the defective site of a tooth, and embedding the artificial tooth root.

The impression obtaining step S12 by means of an impression coping is a step of obtaining an impression by means of an impression coping, after the embedded artificial tooth root sufficiently joins to the jawbone. The impression obtaining by means of an impression coping may be carried out by a known method.

The analog model forming step S13 is a step of attaching an analog to the impression obtained by the impression obtaining step S12 by means of the impression coping, and to the impression coping in the impression, and based on the impression and the coping, producing a plaster model. That is, an analog model which is a plaster model in which the analog is embedded is formed.

To the analog of the analog model, the disposition of the artificial tooth root of the patient is transferred with a good accuracy.

Figure 5:
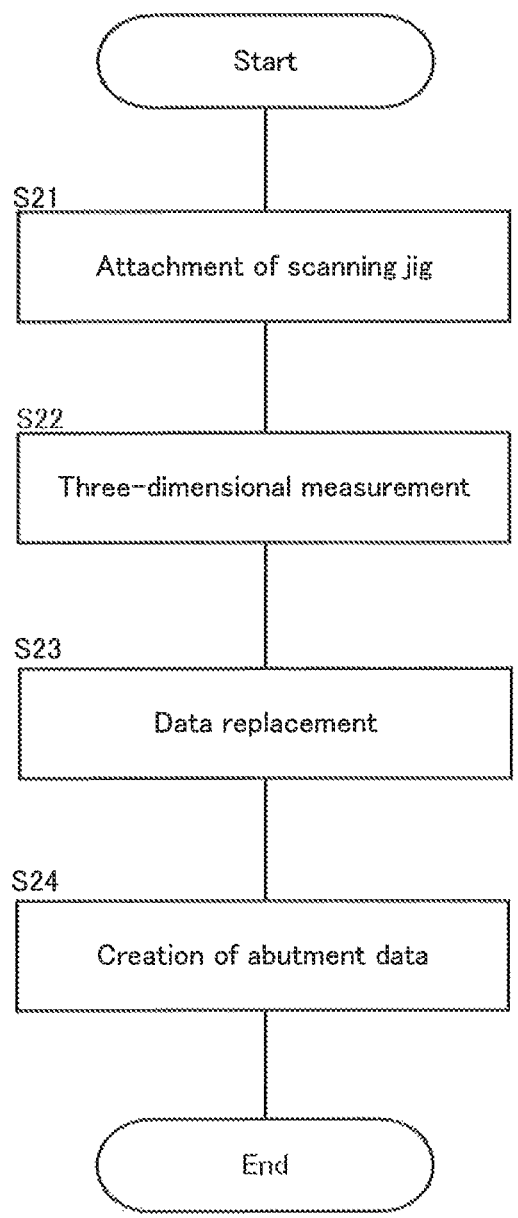
FIG. 5 is a flowchart to explain a creating step of a three-dimensional data.

The explanation will be continued going back to FIG. 3. The three-dimensional data creating step S20 is a step of making a three-dimensional shape data of the abutment to be produced. The three-dimensional data creating step S20 may be carried out as shown in FIG. 5 for example. FIG. 5 shows a flow of the three-dimensional data creating step S20. That is, the three-dimensional data creating step S20 includes a scanning jig attachment step S21, a three-dimensional measurement step S22, a data replacement step S23, and an abutment data creating step S24.

The scanning jig attachment step S21 is a step of attaching the scanning jig 10 described above to the analog model produced in the analog model producing step S10. The order and the like of the step are schematically shown by drawings of FIGS. 6 to 9.

Figure 6:
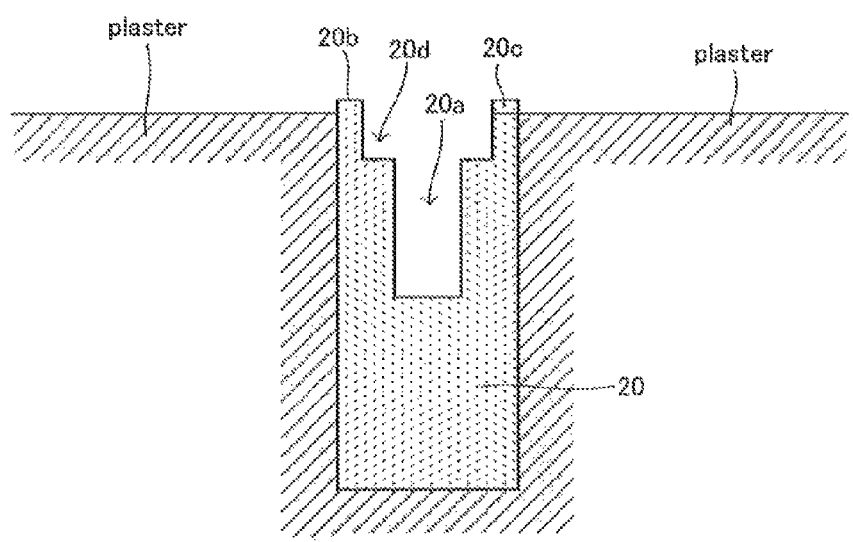
FIG. 6 is a view to explain an attachment step of the scanning jig.

FIG. 6 schematically shows a configuration of the analog 20 embedded in the analog model.

The analog 20 is also a member formed in a bottomed cylindrical shape provided with a bottom only on one side, and the hollow part 20a is formed thereinside. A female screw groove is formed in the hollow part 20a so that the fixation member 12 of the scanning jig 10 can be threaded.

In the end surfaces of the analog 20 in the longitudinal direction, a surface having an opening communicating to the hollow part 20a becomes an end surface 20b having contact with the end surface 11e which functions as the position determination means in axial direction of the main body 11 of the scanning jig 10. Also, a part of the end surface 20b is provided with a groove 20c in a manner to cut a cylindrical wall part of the analog 20 in the radial direction.

Further, from a part of the end surface 20b, a fitted part 20d cut off in a manner to be dug down along with the longitudinal direction of the analog 20 is formed.

As can be seen from FIG. 6, the analog 20 is embedded in the plaster configuring an external appearance of the analog model. Therefore the embedded angle and depth of the analog 20 cannot be seen from the external appearance of the analog model.

Figure 7:
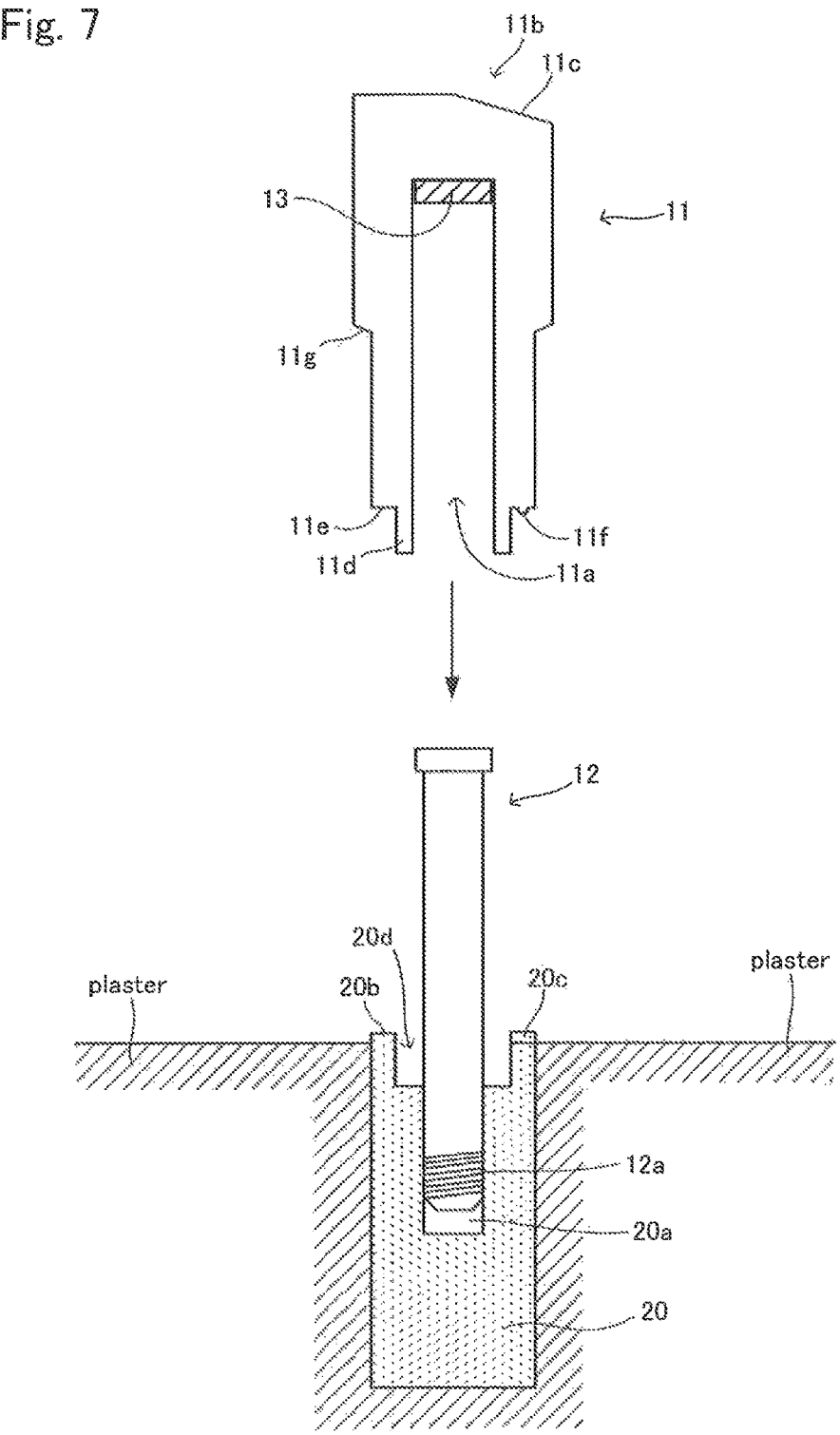
FIG. 7 is another view to explain the attachment step of the scanning jig.

To the analog 20 installed to the analog model, as shown in FIG. 7, the fixation member 12 is attached such that the one end side of the fixation member 12 where the screw part 12a is arranged is threaded. This is carried out by threading the screw part 12a of the fixation member 12 to the female screw groove formed to the hollow part 20a.

Next, as shown by a straight arrow in FIG. 7, the main body 11 is installed in a manner to put it on the fixation member 12 standing on the analog 20. In this regard, the other end side of the fixation member 12 where the screw head is arranged is inserted to the hollow part 11a of the main body 11.

Figure 8:
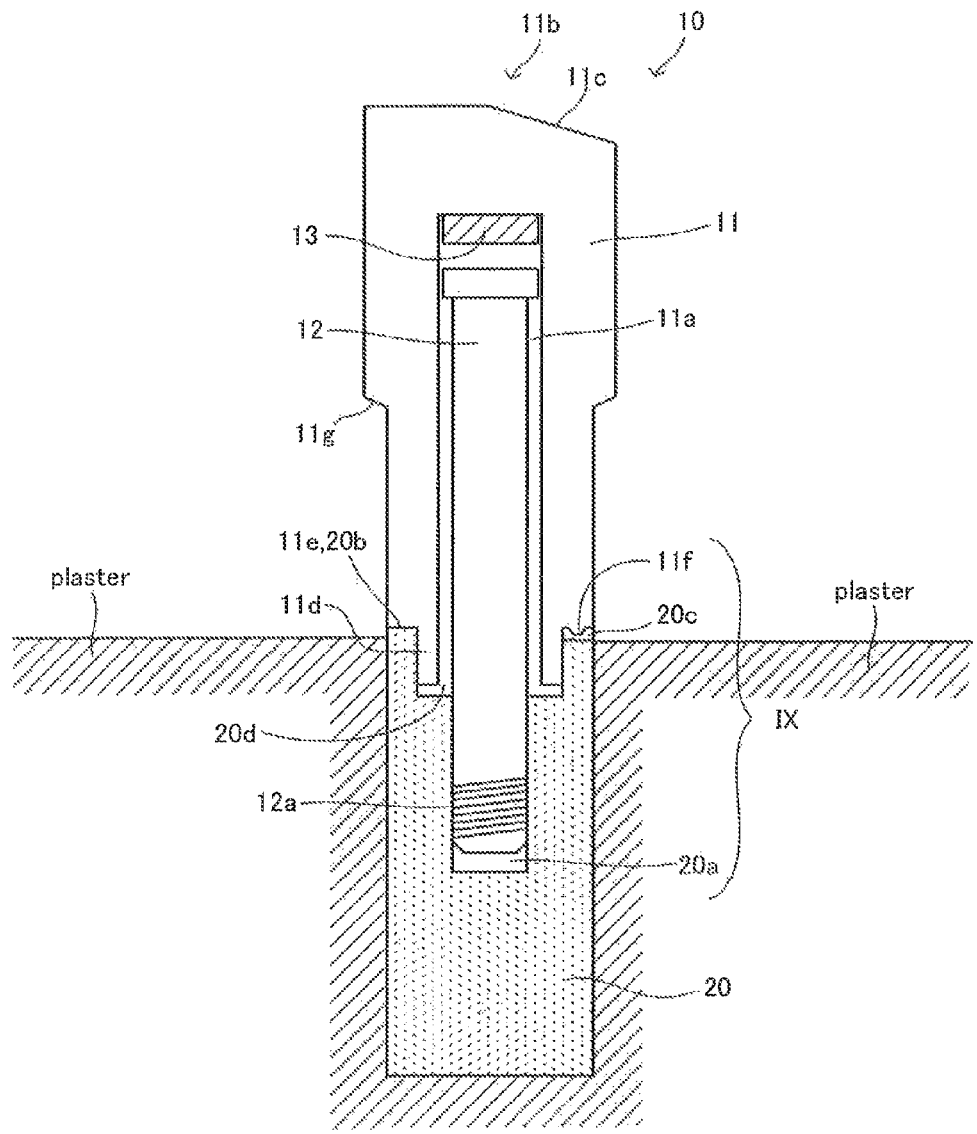
FIG. 8 is a view showing a situation in which the scanning jig is attached to the analog.
Figure 9:
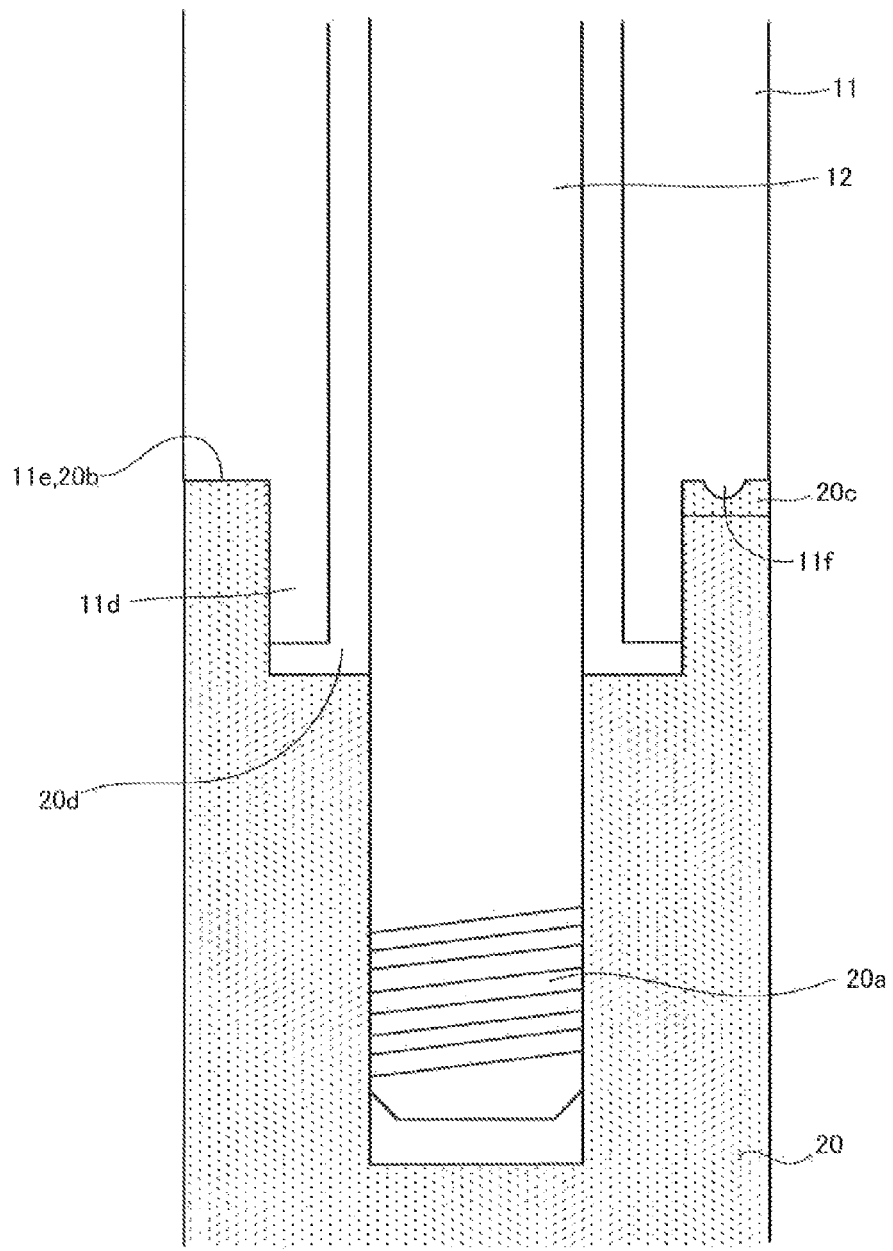
FIG. 9 is an enlarged view of a part shown by IX in FIG. 8.

FIG. 8 is a schematic view of a situation in which the scanning jig 10 is attached to the analog model as described above. FIG. 9 is an enlarged view of a portion shown by IX in FIG. 8. As can be seen from FIGS. 8 and 9, regarding the axial direction of the main body 11, the position in the axial direction of the main body 11 is determined only by the end surface 11e as the position determination means in axial direction having contact with the end surface 20b of the analog 20. Therefore, the end surface of the fitting part 11d does not have contact with the analog 20, and the main body 11 and the magnet 13 do not have contact with the fixation member 12 in the axial direction.

Also, regarding the rotational direction of the main body 11, the position of the main body 11 in the rotational direction is determined only by the protrusion 11f as the position determination means in rotational direction entering inside the groove 20c of the analog 20.

Further, regarding the radial direction of the main body 11, the position of the main body 11 in the radial direction is determined only by the fitting part 11d as the position determination means in radial direction getting inserted to the fitted part 20d of the analog 20.

As described above, only by each position determination means, each of the position determinations in the axial direction, in the rotational direction, and in the radial direction is carried out at the one contacting portion (position determination means) to the analog 20. Therefore each position determination is not affected by the other portions, whereby it is possible to improve accuracy of the position determination.

Also, since the main body 11 can be arranged only by putting it on the fixation member 12, and the main body 11 and the fixation member 12 are arranged stably by the attractive force of the magnet 13 without requiring any fixation by a screw or the like, easy disposition and stable attachment can be realized. Here, the magnet 13 and the fixation member 12 do not have a direct contact with each other. However, since they are arranged close to each other, the attractive force works between them.

With a scanning jig fixated to an analog or an artificial tooth root with a screw as the conventional technique, degree of the fixation force with the screw differs depending on users. If the force to thread the screw is too strong, the scanning jig sinks to the analog or the artificial tooth root, or the fitting part becomes deformed, whereby there is a possibility of causing an error. In contrast, since the scanning jig 10 according to the present invention is fixated by the magnetic force, it is possible to even out the force to fixate the scanning jig, thereby not causing the error occurred in the conventional technique.

As described above, the scanning jig 10 is arranged in a manner to project from the analog model in a direction extending the analog 20 embedded inside the analog model, then the analog 20 to which the scanning jig 10 is attached is formed, whereby it becomes possible to obtain the embedded posture of the analog 20.

In this regard, it is preferable that a model of the gum in the analog model is removed.

Going back to FIG. 5, the explanation will be continued. The three-dimensional measurement step S22 is a step of measuring three-dimensionally the shape of the analog model to which the scanning jig 10 is attached. This makes it possible to obtain the shapes of the analog model and the scanning jig 10 attached to the analog model as three-dimensional shape data. Here, a general three-dimensional measuring apparatus can be used.

The data replacement step S23 is a step of replacing a corresponding portion of the three-dimensional shape data obtained in the three-dimensional measurement step S22, with a three-dimensional shape data of the artificial tooth root and a three-dimensional shape data of the scanning jig that are prepared in advance. That is, the three-dimensional shape data of the scanning jig prepared in advance is replaced in a manner to apply to the portion where the scanning jig 10 is arranged in the three-dimensional shape data of the analog model. Also, the three-dimensional shape data of the artificial tooth root prepared in advance is applied to the portion of the analog 20 which can be obtained from the scanning jig 10. A known method can be applied for this replacement.

Since the scanning jig 10 is used here, the end surface 11b including the inclined surface 11c of the scanning jig 10 has a large dimension, and the replacement accuracy in the axial direction (longitudinal direction) of the scanning jig 10 is improved. The replacement accuracy of data in the rotational direction is also improved because of the shape of the inclined surface 11c.

The abutment data creating step S24 is a step of creating a three-dimensional shape data of an abutment suitable for the patient, based on the obtained three-dimensional shape data.

Since the replacement is carried out with a good accuracy especially in the data replacement step S23, the improvement in accuracy is adequately reflected to the abutment data as well, whereby it is possible to create the abutment data more conformed to the patient.

Going back to FIG. 3, the explanation of the abutment manufacturing method S1 will be continued. The abutment producing step S30 is a step of producing an abutment based on the three-dimensional data created in the three-dimensional creating step S20 described above. In this step, a known method can be applied. For example, by providing the three-dimensional data to an NC machine tool such as a machining center, it is possible to produce an abutment with a high accuracy.

Figure 10:
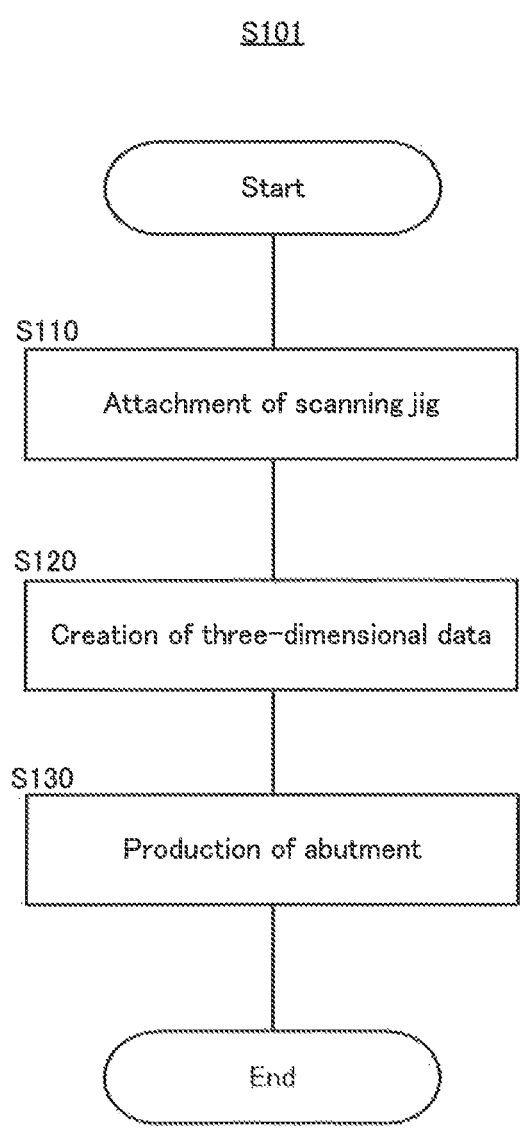
FIG. 10 is a flowchart to explain another example of manufacturing steps of the abutment.

Next, an abutment manufacturing method S101 which is another example of method for manufacturing an abutment using the scanning jig 10 is described. This one is a method for manufacturing an abutment using the scanning jig 10 directly to the artificial tooth root 30 embedded inside the oral cavity. FIG. 10 shows a flow of the abutment manufacturing method S101. As can be seen from FIG. 10, the abutment manufacturing method S101 includes a scanning jig attachment step S110, a three-dimensional data creating step S120, and an abutment producing step S130. Hereinafter, each step is described.

Figure 11:
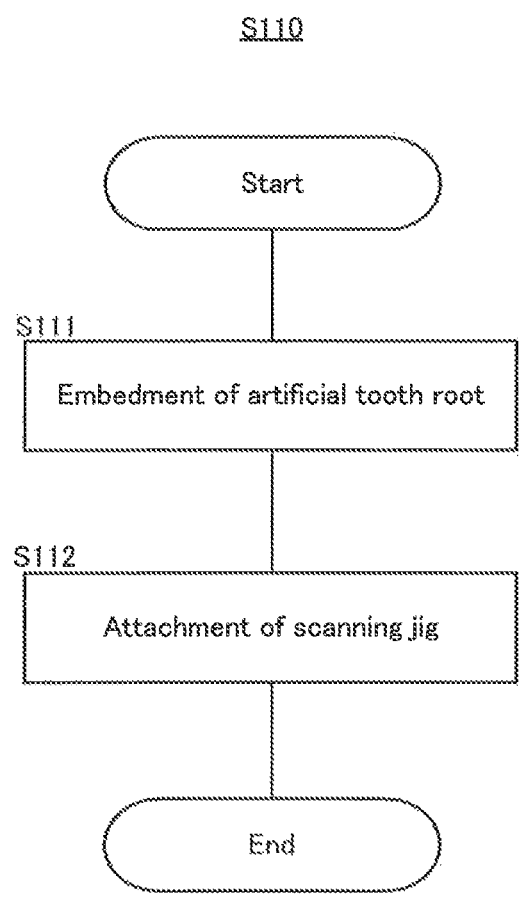
FIG. 11 is a flowchart to explain an attachment step of the scanning jig.

The scanning jig attachment step S110 is a step of attaching the scanning jig 10 to the artificial tooth root 30 embedded inside the oral cavity. FIG. 11 shows a flow of the scanning jig attachment step S110. That is, the scanning jig attachment step S110 includes an artificial tooth root embedding step S111 and a scanning jig attachment step S112.

The artificial tooth root embedding step S111 is a step of creating a hole to embed the artificial tooth root 30 to a jawbone at a defective site of a tooth, and embedding the artificial tooth root 30.

Figure 12:
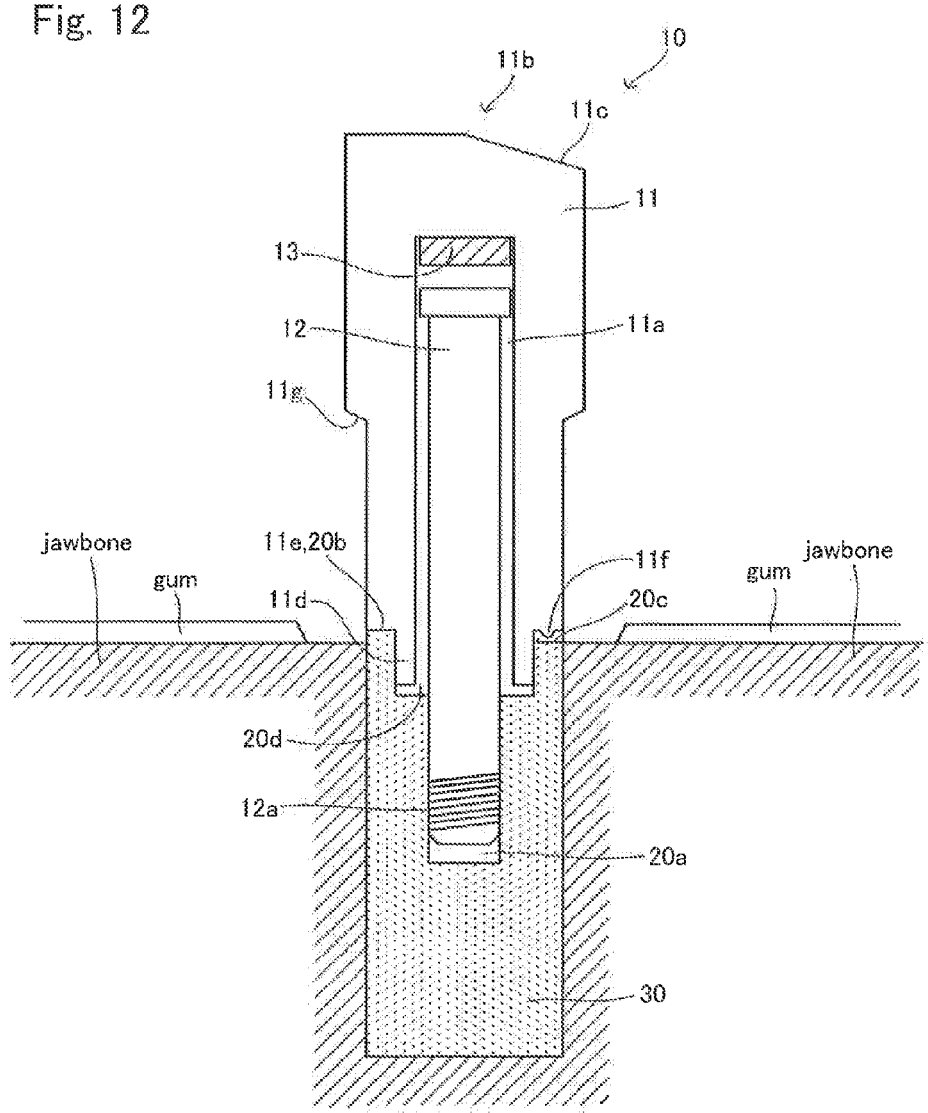
FIG. 12 is a schematic view showing a situation in which the scanning jig is attached to the artificial tooth root in an oral cavity.

The scanning jig attachment step S112 is a step of attaching the scanning jig 10 to the embedded artificial tooth root 30 after the artificial tooth root 30 is sufficiently joined to the jawbone. Procedure of attachment of the scanning jig 10 to the artificial tooth root 30 is same as in the scanning jig attachment step S21 described above, and the scanning jig 10 is attached to the artificial tooth root 30 instead of to the analog 20. The artificial tooth root 30 has an almost same shape as the analog 20 except a slight difference in shape, material and the like. FIG. 12 shows a schematic view of a situation in which the scanning jig 10 is attached to the artificial tooth root 30. In FIG. 12, for a portion of the artificial tooth root 30 having the same shape as in the analog 20, a same symbol as in the analog 20 is given.

This makes it possible to form the artificial tooth root 30 to which the scanning jig is attached. The scanning jig 10 is arranged in a manner to project from the gum in a direction extending the artificial tooth root embedded inside the oral cavity. Therefore it becomes possible to measure the artificial tooth root 30.

Figure 13:
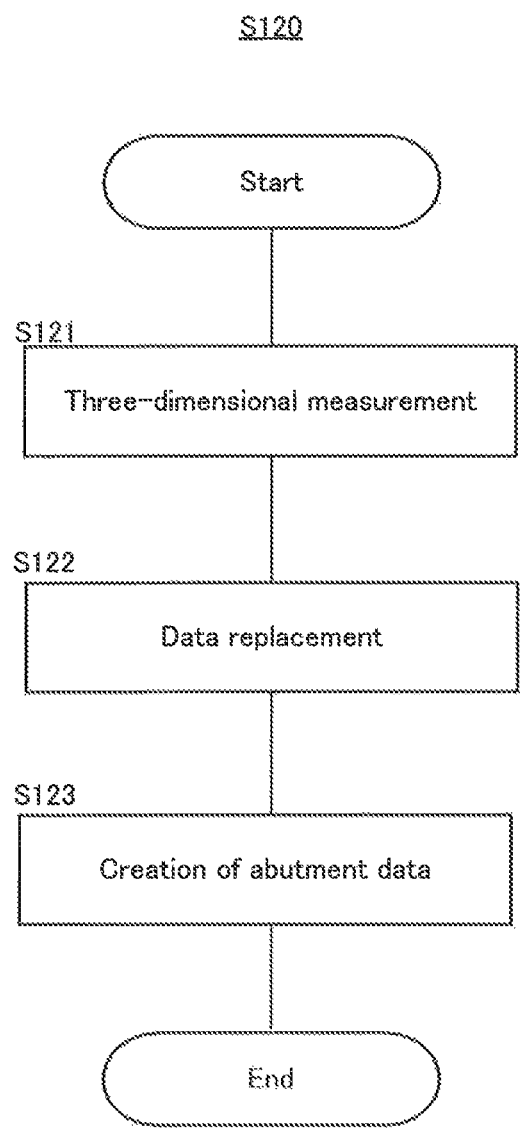
FIG. 13 is a flowchart to explain a creating step of the three-dimensional data.

The explanation of the abutment manufacturing method S101 will be continued going back to FIG. 10. The three-dimensional data creating step S120 is a step of creating a three-dimensional shape data of the abutment to be produced. The three-dimensional data creating step S120 can be carried out as shown in FIG. 13 for example. That is, the three-dimensional data creating step S120 includes a three-dimensional measurement step S121, a data replacement step S122, and an abutment data creating step S123.

The three-dimensional measurement step S121 is a step of carrying out a three-dimensional measurement of a surface configuration of inside of the oral cavity where the scanning jig 10 is attached. This step makes it possible to obtain the shape of the surrounding of the area in the oral cavity where the scanning jig 10 is attached, and the shape of the scanning jig 10 attached inside the oral cavity can be obtained as three-dimensional data. The three-dimensional data of inside of the oral cavity can be obtained by means of a three-dimensional measurement apparatus for inside of oral cavity.

The data replacement step S122 is a step of replacing the corresponding portion of the three-dimensional data obtained in the three-dimensional measurement step S121, with a three-dimensional shape data of the artificial tooth root and a three-dimensional shape data of the scanning jig 10 prepared in advance. That is, the three-dimensional shape data of the scanning jig prepared in advance is replaced in a manner to apply to the portion where the scanning jig is arranged in the three-dimensional data of the inside of the oral cavity. Also, the three-dimensional data of the artificial tooth root prepared in advance is applied to the portion of the artificial tooth root whose position can be obtained because the artificial tooth root is fitted with the scanning jig.

Since the scanning jig 10 is used here, the end surface 11b including the inclined surface 11c of the scanning jig 10 has a large dimension, whereby the replacement accuracy of the scanning jig 10 in the axial direction (longitudinal direction) is improved. Also, the shape of the inclined surface 11c makes it possible to improve the data replacement accuracy in the rotational direction, and to obtain information such as the kind of the artificial tooth root embedded to the patient.

The abutment data creating step S123 is a step of creating a shape data of the abutment which is suitable to the patient, based on the obtained three-dimensional shape data. Since the replacement is carried out with a good accuracy especially in the data replacement step S122, the improvement in accuracy is adequately reflected to the abutment data, whereby it is possible to create the abutment data matched well to the patient.

The explanation of the abutment manufacturing method S101 will be continued going back to FIG. 10. The abutment producing step S130 is a step of producing an abutment based on the three-dimensional shape data created in the three-dimensional data creating step S120 described above. In this step, for example, an abutment is produced with a high accuracy by providing the three-dimensional data to an NC machine tool such as a machining center.

Figure 14:
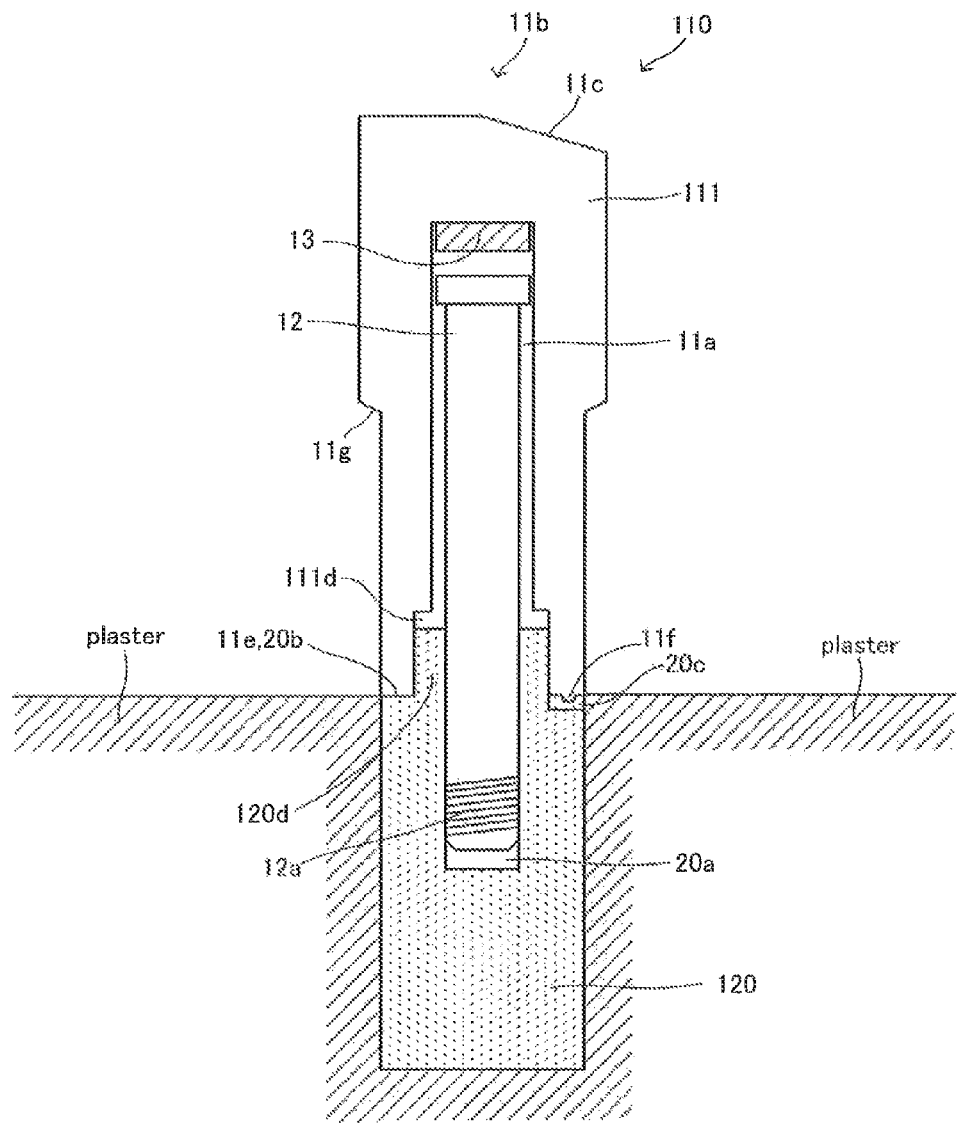
FIG. 14 is a cross-sectional view of a scanning jig according to another embodiment, the view corresponding to FIG. 8.

FIG. 14 shows a situation in which the scanning jig 110 according to another embodiment is attached to an analog model in which an analog 120 is embedded. FIG. 14 is a view seen from the same viewpoint as in FIG. 8.

The scanning jig 10 described above has a configuration in which the fitting part 11d is projected from a part of the end surface 11e of the main body 11 and the fitted part 20d is formed to the analog 20, the fitted part 20d being cut off so that the fitting part 11d can be inserted.

In contrast, in the scanning jig 110 of this embodiment, the fitted part 111d is formed in a manner to be cut off in the axial direction on a hollow part 11a side of the end surface 11e of a main body 111. The protrusion 11f is formed to a part of the end surface 11e as in the scanning jig 10. On the other hand, a fitting part 120d having a cylindrical shape is provided to a part of the end surface 20b of the analog 120 in a direction extending the analog 120 from a hollow part 20a side. Also, a groove 20c for inserting the protrusion 11f is provided to a part of the end surface 20b.

This configuration of the scanning jig 110 is based on the configuration of the end portion of the analog 120. That is, as can be seen from FIG. 14, the basic structure of the analog

120 is same as that of the analog 20 described above. However, since the analog 120 is provided with the projecting fitting part 120*d*, corresponding to the fitting part 120*d*, a fitted part 111*d* is provided to a main body 111 side of the scanning jig 110. The scanning jig 110 described above exerts the same effect as that of the scanning jig 10, for example the end surface of the fitting part 120*d* does not have contact with the main body 111.

DESCRIPTION OF THE REFERENCE NUMERALS

10 scanning jig
11 main body
12 fixation member
13 magnet

The invention claimed is:

1. A scanning jig for attaching to an analog embedded in a model or to an artificial tooth root embedded inside an oral cavity, the scanning jig comprising:
   a main body formed in a bottomed cylindrical shape provided with a bottom to one end portion;
   a fixation member of which one end side is inserted inside the cylindrical shape of the main body and the other end side is fixated to the analog or the artificial tooth root; and
   a magnet arranged inside the cylindrical shape of the main body, the magnet being arranged in a position where the magnet does not have contact with the fixation member,
   wherein:
   the main body is not provided with a hole or a groove on an end surface at side provided with the bottom in an axial direction of the cylindrical main body;
   the end surface is provided with an inclined surface that is inclined with respect to the axial direction of the cylindrical main body; and
   a cylindrical fitting part extends from the main body in the axial direction and is provided for a second end portion of the main body at a side opposite from the bottom.

2. The scanning jig according to claim 1, wherein
   for a cylindrical axis direction of the main body, the main body is, with a state of being attached to the analog or the artificial tooth root, configured such that only the fitting part has contact with the analog or the artificial tooth root.

* * * * *